(12) United States Patent
Lange et al.

(10) Patent No.: US 9,110,051 B2
(45) Date of Patent: Aug. 18, 2015

(54) PHARMACOLOGIC METHOD OF LOWERING CHOLESTEROL PRODUCTION

(75) Inventors: Yvonne Lange, Chicago, IL (US); Theodore L. Steck, Chicago, IL (US)

(73) Assignees: The University of Chicago, Chicago, IL (US); Rush University Medical Center, Chicago, IL (US)

( * ) Notice: Subject to any disclaimer, the term of this patent is extended or adjusted under 35 U.S.C. 154(b) by 0 days.

(21) Appl. No.: 13/594,564

(22) Filed: Aug. 24, 2012

(65) Prior Publication Data
US 2012/0322091 A1    Dec. 20, 2012

Related U.S. Application Data

(62) Division of application No. 10/599,898, filed as application No. PCT/US2005/012628 on Apr. 13, 2005, now abandoned.

(60) Provisional application No. 60/561,585, filed on Apr. 13, 2004.

(51) Int. Cl.
*C12Q 1/60* (2006.01)
*G01N 33/50* (2006.01)
*G01N 33/80* (2006.01)
*G01N 33/92* (2006.01)

(52) U.S. Cl.
CPC .......... *G01N 33/5014* (2013.01); *G01N 33/502* (2013.01); *G01N 33/5008* (2013.01); *G01N 33/5044* (2013.01); *G01N 33/80* (2013.01); *G01N 33/92* (2013.01); *G01N 2800/044* (2013.01)

(58) Field of Classification Search
None
See application file for complete search history.

(56) References Cited

U.S. PATENT DOCUMENTS

| 4,897,426 | A | 1/1990 | Llinas et al. |
| 6,713,057 | B1 | 3/2004 | Chatterjee |
| 2003/0082617 | A1 | 5/2003 | Rothblat et al. |
| 2004/0022883 | A1 | 2/2004 | Brovelli et al. |

FOREIGN PATENT DOCUMENTS

| JP | 63-104917 | 5/1988 |

OTHER PUBLICATIONS

Lange and Ramos, Analysis of the distribution of cholesterol in the intact cell, 1983, The Journal of Biological Chemistry, 258, 15130-15134.*
Ghoshroy et al., Investigation of Membrane Disruption in the Reaction Catalyzed by Cholesterol Oxidase, 1997, Biochemistry 36, 6133-6140.*
Rottem et al., Isolation of Mycoplasma Membranes by Digitonin, 1972, J. Bacteriol. 110(2): 699-705.*
Lange et al., The effect of cholesterol and other intercalated amphipaths on the contour and stability of the isolated red cell membrane, 1980, Journal of Biological Chemistry 255(19): 9331-9337.*
Durst et al., Tris/Tris• HCl: A standard buffer for use in the physiologic pH range, 1972, Clinical Chemistry 18(3): 206-208.*
Dietschy et al., Thematic review series: brain Lipids. Cholesterol metabolism in the central nervous system during early development and in the mature animal, 2004, Journal of Lipid Research 45(8): 1375-1397.*
Zhang et al., LuXuRies of lipid homeostasis: the unity of nuclear hormone receptors, transcription regulation, and cholesterol sensing, 2002, Molecular Interventions 2(2): 78.*
Chen, Qian et al., "Excess Membrane Cholesterol Alters Human Gallbladder Muscle Contractility and Membrane Fluidity," Gastroenterology, vol. 116, No. 3, (1999), pp. 678-685.
Chen, Shao-Yu et al., "Octanol antagonism of ethanol teratogenesis," The FASEB Journal, vol. 15, (Jul. 2001), pp. 1649-1651.
Christian, Aimee et al., "Use of cyclodextrins for manipulating cellular cholesterol content," Journal of Lipid Research, vol. 38, No. 11, (1997), pp. 2264-2272.
Christian, Aimee E. et al., "Comparison of the capacity of β-cyclodextrin derivatives and cyclophanes to shuttle cholesterol between cells and serum lipoproteins," Journal of Lipid Research, vol. 40, (1999), pp. 1475-1482.
Duncan, James L. et al., "Resistance to Streptolysin O in Mammalian Cells Treated with Oxygenated Derivatives of Cholesterol. Cholesterol Content of Resistant Cells and Recovery of Streptolysin O Sensitivity," Biochimica et Biophysica Acta, vol. 603, (1980), pp. 278-287.
Ehrlich, H. Paul et al., "Cell Coupling Modulates the Contraction of Fibroblast-Populated Collagen Lattices," Journal of Cellular Physiology, vol. 184, (2000), pp. 86-92.
Final Office Action received in U.S. Appl. No. 10/599,898 dated Oct. 27, 2011 (9 pages).
Gilbert, R.J.C., "Pore-forming toxins," Cellular and Molecular Life Sciences, vol. 59, (2002), pp. 832-844.
Heuck, Alejandro P. et al., "Assembly and Topography of the Prepore Complex in Cholesterol-dependent Cytolysins," Journal of Biological Chemistry, vol. 278, No. 33, (Aug. 15, 2003), pp. 31218-31225.
Klein, Uwe et al., Alteration of the Myometrial Plasma Membrane Cholesterol Content with β-Cyclodextrin Modulates the Binding Affinity of the Oxytocin Receptor, Bioichemistry, vol. 34, No. 42, (Oct. 24, 1995), pp. 13784-13793.

(Continued)

*Primary Examiner* — Robert Yamasaki
(74) *Attorney, Agent, or Firm* — McDermott Will & Emery LLP (57) ABSTRACT

The present invention provides a screening method for identifying test agents that modulate cell membrane cholesterol activity. The modulating activity of the test agents may be measured using lytic compounds, which cause cell lysis or increases in cell permeability in response to cell membrane cholesterol levels. The invention further provides therapeutic agents that are identified using the screening method. The therapeutic agents either increase or decrease the cell membrane cholesterol activity, cholesterol concentration and/or both in vivo and/or in vitro.

14 Claims, 3 Drawing Sheets

(56) References Cited

OTHER PUBLICATIONS

Kowalczyk, Andrzej et al., "Potential Misevaluation of the Ground-State Dissociation Constant from Fluorimetric Titrations: Application to the Ion Indicators SBFI, PBFI, and Fura-2," Analytical Biochemistry, vol. 245, (Feb. 1, 1997), pp. 28-37.

Lange, Yvonne et al., "Cholesterol Homeostasis: Modulation by Amphiphiles," The Journal of Biological Chemistry, vol. 269, No. 47, (Nov. 25, 1994), pp. 29371-29374.

Lange, Yvonne et al., "Cholesterol Oxidase Susceptibility of the Red Cell Membrane," Biochimica et Biophysica Acta, vol. 769, (1984), pp. 551-562.

Lange, Yvonne et al., "The role of intracellular cholesterol transport in cholesterol homeostasis," Trends in Cell Biology, vol. 6, (Jun. 1996), pp. 205-208.

Lange, Yvonne et al, "Regulation of endoplasmic reticulum cholesterol by plasma membrane cholesterol," Journal of Lipid Research, vol. 40, (1999), pp. 2264-2270.

Lange, Yvonne et al., "How cholesterol homeostasis is regulated by plasma membrane cholesterol in excess of phospholipids," Proc. Natl. Acad. USA, vol. 101, No. 32, (Aug. 10, 2004), pp. 11664-11667.

Lange, Yvonne, "Tracking Cell Cholesterol with Cholesterol Oxidase," Journal of Lipid Research, vol. 33, (1992), pp. 315-321.

Mukherjee, Sushmita et al., "Cholesterol Distribution in Living Cells: Fluorescence Imaging Using Dehydroergosterol as a Fluorescent Cholesterol Analog," Biophysical Journal, vol. 75, (Oct. 1998), pp. 1915-1925.

Non-Final Office Action received in U.S. Appl. No. 10/599,898 dated Feb. 28, 2012 (13 pages).

Non-Final Office Action received in U.S. Appl. No. 10/599,898 dated May 17, 2011 (19 pages).

Norman, Anthony W. et al., "Polyene Antibiotic-Sterol Interaction," Adv. Lipid Res., vol. 14, (1976), pp. 127-170.

Radhakrishnan, Arun et al., "Chemical Activity of Cholesterol in Membranes," Biochemistry, vol. 39, (2000), pp. 8119-8124.

Radhakrishnan, Arun et al., "Condensed Complexes, Rafts, and the Chemical Activity of Cholesterol Membranes," Proc. Natl Acad Sci, vol. 97, No. 23, (Nov. 7, 2000), pp. 12422-12427.

Ramachandran, Rajesh et al., "Structural insights into the membrane-anchoring mechanism of a cholesterol-dependent cytolysin," Natural Structural Biology, vol. 9, No. 11, (Nov. 2002), pp. 823-827.

Rothblat, George H. et al., "Cell cholesterol efflux: integration of old and new observations provides new insights," Journal of Lipid Research, vol. 40, (May 1999), pp. 781-796.

Salesse, Ronald et al., "Modulation of Adenylate Cyclase Activity by the Physical State of Pigeon Erythrocyte Membrane. 2. Fluidity-Controlled Coupling between the Subunits of the Adenylate Cyclase System," Biochemistry, vol. 21, (1982), pp. 1587-1590.

Schmitt, Clare K. et al., "Bacterial Toxins: Friends or Foes?" Emerging Infectious Disease, vol. 5, No. 2, (Apr.-Jun. 1999), pp. 224-234.

Simons, Kai et al., "How Cells Handle Cholesterol," Science, vol. 290, (Dec. 1, 2000), pp. 1721-1726.

Steck, Theodore L. et al., "Probing Red Cell Membrane Cholesterol Movement with Cyclodextrin," Biophysical Journal, vol. 83, (Oct. 2002), pp. 2118-2125.

Lange, et al, "Cholesterol homeostasis and the escape tendency (activity) of plasma membrane cholesterol," Progress in Lipid Research 47 (2008) 319-332.

* cited by examiner

PHARMACOLOGIC METHOD OF LOWERING CHOLESTEROL PRODUCTION

CLAIM OF PRIORITY

This application is a divisional of U.S. patent application Ser. No. 10/599,898, filed Jul. 19, 2007, which is the National Stage Entry of International Application No. PCT/US2005/012628, filed Apr. 13, 2005, which in turn claims priority to U.S. Provisional Patent Application 60/561,585, filed Apr. 13, 2004, the entire contents of which are incorporated by reference in their entireties.

STATEMENT REGARDING FEDERALLY SPONSORED RESEARCH

This invention was made with Government support under grant No. HL 28448 awarded by the National Institutes of Heath. The Government has certain rights in this invention.

FIELD OF INVENTION

The present invention relates to methods and compounds that modulate cholesterol levels as well as screening methods used to identify such compounds.

BACKGROUND OF THE INVENTION

Cholesterol is an essential constituent of all animal cell membranes. Cholesterol reduces the permeability of the membrane, increases the membrane's mechanical strength and helps to organize the membrane constituents laterally into domains. In the cell, cholesterol's abundance is tightly controlled through biosynthetic, storage, ingestion, and transfer pathways. Through these pathways, cells have the ability to adjust their cholesterol level to their needs.

Unfortunately, in some instances, in vivo cholesterol levels are not properly adjusted. Cholesterol disorders, specifically high serum levels of cholesterol and the mishandling of cholesterol in cells of arterial walls, may cause disease and death in humans by contributing to the formation of atherosclerotic plaques in arteries throughout the body. In fact, cholesterol disorders in the United States contribute to such a high number of health issues that the National Heart, Lung, and Blood Institute launched the National Cholesterol Education Program in 1985. The goal of the National Cholesterol Education Program is to contribute to reducing illness and death from coronary heart disease in the United States by reducing the percent of Americans with high blood cholesterol. The program plans to do this by raising awareness of the link between high cholesterol levels and coronary heart disease.

Many of the illnesses triggered by cholesterol abnormalities are addressed through both increased education and drug treatment. Current drugs used for treatment of cholesterol related disorders are compounds called statins, which inhibit cholesterol biosynthesis by blocking the production of the cholesterol precursor, mevalonic acid. However, mevalonic acid is used by the body to synthesize many other important cellular constituents. Unfortunately, because of the numerous cellular uses for mevalonic acid, statins, which are largely non-specific, often have side effects because they suppress a variety of metabolic functions other than cholesterol biosynthesis.

Accordingly, there is need to find other therapeutic agents to combat cholesterol disorders as well as methods for identifying such compounds.

SUMMARY OF THE INVENTION

One embodiment of the present invention provides a method of screening compounds for cholesterol modulating activity. The screening method involves contacting one or more test agents with one or more cells and determining or measuring whether the one or more test agents has an effect on cholesterol activity, cholesterol concentration or both in a membrane of the one or more cells. The screening method can also involve contacting the one or more cells with a lytic compound, so that the lytic compound causes perforation or lysis of the membrane of the one or more cells when the cholesterol activity, cholesterol concentration or both of the membrane of the one or more cells reaches a level at or above a threshold cholesterol level. In certain screening methods, the cholesterol content of the membrane can be increased or decreased by contacting the one or more cells with a cholesterol modulating compound.

In one embodiment, the invention includes a method of screening compounds for cholesterol modulating activity by contacting test agents with cells and determining whether the test agents has an effect on cholesterol activity, cholesterol concentration or both in the cell membrane.

In a further embodiment, determining whether the one or more test agents has an effect on cholesterol activity, cholesterol concentration or both in the cell membrane includes contacting the cells with a lytic compound that causes perforation or lysis of the membrane of the cells when the cholesterol activity, cholesterol concentration or both of the membrane of the cells reaches a level at or above a threshold cholesterol level.

In yet another embodiment, the cholesterol content of the membrane may be either increased or decreased by contacting the cells with a cholesterol modulating compound. In some embodiments, this will be performed prior to, simultaneous with or subsequent to contact with the test agents.

In another embodiment, the invention includes a method of identifying a compound that modulates cholesterol activity by identifying test agents that modulate the cholesterol activity in a cell membrane, where the test agents has been identified by a method in any one of the preceding paragraphs.

In a further embodiment, the invention comprises a method of manufacturing a compound that modulates cholesterol activity by synthesizing or isolating therapeutic agents identified by the methods of identifying a compound that modulates cholesterol activity.

In yet a further embodiment, the invention includes a method of modulating the cholesterol level of a cell by contacting cells with an effective amount of octanol, ceramide, diglyceride, lysophosphatidyl choline, or a combination thereof, thereby increasing or decreasing the cholesterol level of the cells. In certain cases, the cells will be in vivo, while in other cases, the cells will be in vitro.

A specific embodiment of the invention includes a kit for determining the effect of a test agent on the cholesterol activity, cholesterol concentration and/or both in a cell membrane. The kit may includes the instructions for carrying out the method of any one of the previous paragraphs and one or more needed reagents.

BRIEF DESCRIPTION OF THE DRAWINGS

FIG. 1 shows the screening of lysis of red blood cells using amphotericin B by turbidity. Human red blood cells were either freshly drawn or taken from an outdated blood bank source and then washed and suspended in physiological buffer. The cholesterol content of washed human red blood cells was varied with methyl-β-cyclodextrin/methyl-β-cyclodextrin-cholesterol complexes. The cells were distributed into a 96-well plate and incubated for a few minutes with saline (O), 0.2 μmol/well octanol (V) or 1 μg/well lysophosphatidylcholine (□). Amphotericin B (20 μg/well) was added and the plate incubated for 1 hour at room temperature. As shown in FIG. 1, the variation of endogenous cholesterol content by methyl-β-cyclodextrin/methyl-β-cyclodextrin-cholesterol complexes, results in cells that will not be lysed by amphotericin B unless a test agent increases the cholesterol concentration, cholesterol activity and/or both in the cell membrane. In FIG. 1, turbidity (signifying intact cells) was determined in a plate-reading photometer as optical density (OD) at 500 nm; loss of OD signifies lysis. In FIG. 1, results are plotted versus total human red blood cell cholesterol, assessed with Amplex™ Red, Molecular Probes, Eugene, Oreg. The cholesterol content of unmodified red blood cells was 0.55 μg/μl cells, close to the threshold of the control curve.

FIG. 2 shows a visual screen of red blood cell lysis caused by amphotericin B. The experiment was as in FIG. 1. Cells with modified cholesterol were placed in the conical wells of a 96-well plate, briefly pre-incubated with the two test compounds, and then treated with amphotericin B (20 μg/well) for one hour at room temperature. The plate was photographed after the cells settled. Row A: saline control. Cells depleted of cholesterol (wells 1-6) resisted lysis (seen as a loss of the central button). Row B: n-octanol (0.2 μmol/well). Even cholesterol depleted cells were lysed by amphotericin B in the presence of octanol but not in controls without amphotericin B (not shown). Row C: Lysophosphatidylcholine (1 μg/well). Even enriched cells resisted amphotericin B lysis.

DETAILED DESCRIPTION

Described herein are compounds and methods for modulating cholesterol levels. Also provided are methods for screening compounds, for example test agents, for their ability to modulate cholesterol levels, both systemically and in cells.

One embodiment described herein provides a method of screening compounds for cholesterol modulating activity. Such a method involves exposing a cell to a compound, such as a test agent, and measuring the cholesterol level of the cell or certain cellular components, such as the plasma membrane, which contains the highest amount of cellular cholesterol, or endoplasmic reticulum, to determine the effect the compound has on the cholesterol levels of the cell or cellular component. Cholesterol level can be reflected as cholesterol activity, cholesterol content and/or cholesterol concentration, as desired. As used herein, a test agent is a chemical compound that has no known modulating effect on a cell's cholesterol level or cholesterol activity. Accordingly, one skilled in the art will understand that the term test agent is dependent on multiple factors including at least the compound to be tested and the cell that is used. The effect the compound has, if any, on the cholesterol activity of the cell can be correlated with cholesterol modulating properties for the compound.

One method for measuring the cholesterol level of the cell includes contacting the cells with a lytic compound that results in disruption of cholesterol containing membranes and determining whether the cell membrane has been disrupted or lysed. In this embodiment, the test compound can be washed away from, or left in contact with, the cell prior to contact with the lytic agent as desired. The degree of cell lysis can also be measured as not all of the cells may lyse. Typically, the lytic compounds will disrupt the cholesterol containing membrane when the cholesterol level of the membrane is at or above a threshold level, below which little or no cell lysis will occur. As such, lysis of the cell membrane provides an indication that the cholesterol level of the cell membrane is at or above the threshold level. In some embodiments, the lytic compounds can have a threshold value that lies near the normal physiological level of the cell used in the assay. Red blood cells typically have a cholesterol content of approximately 0.8 moles per mole phospholipids or 0.25 mg cholesterol per mg membrane protein. Cultured human fibroblasts typically contain approximately 30 μg cholesterol per mg cell protein. Factors that might affect the threshold level of a lytic agent might be the lipid composition of the cells, the type and concentration of drugs added to alter the threshold and experimental conditions such as incubation temperature and time of exposure. Examples of lytic compounds that are suitable for use in the present methods include lysophosphatides (monoacyl derivatives of diacyl phospholipids), antibiotics, such as polyene antibiotics, and cholesterol oxidase. Exemplary of lysophosphatides is lysophosphatidyl choline. Suitable examples of polyene antibiotics include Amphotericin B, Amphotericin A, Amycin, Ayfactin, Azalomycin F, Candicidin A, Candicidin B, Candimycin, Copiamycin, Filipin, Flavofungin, Fradicin, Hamycin, Lucensomycin, Lucknomycin, Mediocidin, Mepartricin, Mepartricin B, Natamycin, Niphimycin, Nystatin Antibiotic Complex, Partricin, Partricin A, Partricin B, Pentamycin, Perimycin A, Proticin, Rimocidin, Sistomycosin, and Sorangicin A. The threshold level for amphotericin B induced lysis is in the range of the membrane cholesterol level, on a molar basis. Bacterial toxins, particularly those that target cholesterol or the plasma membrane, may also be used as lytic compounds. Bacterial toxins that may be used as lytic compounds include perfringolysin O from *Clostridium perfringens*, hemolysin from *Escherichia coli*, listeriolysin O from *Listeria monocytogenes*, α-toxin from *Staphyloccocus aureus*, pneumolysin from *Streptococcus pneumoniae*, and streptolysin O from *Streptococcus pyogenes*. Such bacterial toxins are discussed in the following: Heuck et al., J Biol. Chem. 2003 Aug. 15; 278(33):31218-25; Ramachandran et al., Nat Struct Biol. 2002 November; 9(11):

823-7; Schmitt et al., Emerg Infect Dis. 1999 March-April; 5(2):224-34; and Gilbert R J., Pore-forming toxins. Cell Mol Life Sci. 2002 May; 59(5):832-44. Sterol-specific lysins, such as saponins may also be used. One skilled in the art will be able to appreciate that any lytic compound which causes cell lysis based on cholesterol level is suitable for use herein, regardless of the mechanism of action such lytic compound uses. Depending upon the cholesterol level of the cells used, the lytic agent can be added before, simultaneous with, or subsequent to cell exposure to the test compound. For example, if the cholesterol level of the cell is below the threshold value for the lytic agent then the lytic agent can be present the entire time whereas if the level is above the threshold value then the lytic agent should be added after the cell has been exposed to the compound being tested. Cell that have cholesterol levels above or below the threshold level can be used and will generally depend on whether an increase or decrease or cholesterol level may be expected.

Regardless of the type of lytic compound, cellular lysis and/or increased cellular permeability may be measured using a variety of methods. In one instance, cell permeability can be measured by a release of ions with an ion indicator, such as SBFI (sodium ions), PBFI (potassium ions) and/or Fura-2 (calcium ions) and in particular the cell impermeable forms of these indicators. See, e.g., Kowalczyk et al. Anal Biochem. 1997 Feb. 1; 245(1):28-37. Additionally, cell turbidity can be measured, such as with a photometer or by eye. Generally, loss of turbidity reflects cell lysis. Cell permeability and lysis can also be measured using dye exclusion assays, where cells with an intact membrane are able to exclude the dye while cells without an intact membrane take up the dye. Suitable exclusion dyes include trypan blue, erythrosin and naphthalene black. A dye uptake stain can be used to measure viability as well. In this case, the dye is normally taken up by viable cells but not by the non-viable cells. Diacetyl fluorescein is an example of a dye used for dye uptake assays.

Other methods of measuring cell lysis include quantifying release of radiolabels from cells following cell lysis and/or an increase in cellular permeability. Tritium or chromium are commonly used radiolabels. The release of radiolabels from lysed cells and/or cells with increased membrane permeability may be measured in various ways including scintillation counting and/or film exposure. Additionally, release of measurable enzymes can indicate cell lysis. Enzymes such as lactate dehydrogenase (LDH) are released from cells that have undergone lysis and/or increases in cellular permeability. One way to measure the presence of lactate dehydrogenase may be to use a colorimetric or fluorometric assay such as CytoTox-ONE™, Promega, Madison, Wis. For numerous detailed methods that can be used to measure cell lysis and/or increases in cellular permeability, see Reed, J. C, Ed., Methods in Enzymology Volume 322: Apoptosis (2000).

Additional methods for measuring cholesterol levels include cell homogenization or fractionation, such as with a sucrose gradient as discussed in Lange et al. J. Lipid Res. 40, 264 (1999) or Chen et al. Gastroenterology. 116(3):678-85 (1999). An example of an approach to measuring overall or plasma membrane cholesterol is the use of the enzyme cholesterol oxidase with detection of the product with, for instance, Amplex™ Red, Molecular Probes, Eugene, Oreg. Total cholesterol levels can also be detected by pelleting and extracting the plasma membrane in chloroform/methanol and separating the organic extract by thin layer chromatography (TLC). Following separation by TLC, cholesterol may be revealed by spraying the TLC plate with $FeCl_3$ and heating to 100° C. for 3-5 minutes. Moreover, cholesterol levels may be determined using insulin receptor (IR) phosphorylation or cholesterol specific binding agents, such as filipin, which can be labeled. See, e.g. Mukherjee et al., Biophys J. 1998 October; 75(4):1915-25. More accurate and precise are analysis with high-performance liquid chromatography (HPLC) or gas-liquid chromatography (GC).

Types and sources of cells that can be used in the described methods are not limited as long as the cell contain cholesterol whose level can be modulated. Accordingly, cells from a wide variety of sources can be used, including both eukaryotic and prokaryotic cells. Typically, the cells will be eukaryotic cells, such as fungal cells or animal cells. When animal cells are used they can be mammalian cells, such as ungulate cells, rodent cells, canine cells, feline cells, porcine cells, and/or aritiodactyla cells. In some embodiments, mammalian cells will be primate cells, for example human, ape, prosimian and/or monkey cells. Fungal cells used in the screening method may include zygomycetes, ascomycetes, basidiomycetes, and/or mycomycotes.

Suitable types of cells that can be used in the methods, include blood cells, both red and white, tissue cells, organ cells, skin cells, connective tissue cells, and the like. Typically, cells that have a determined level of cholesterol in their cellular components will be used to simplify interpretation of the data. In some embodiments, cells with vigorous cholesterol homeostasis, such as fibroblasts, hepatoma cells or macrophages can be used so that a compounds effect on cholesterol homeostasis can be measured. Vigorous cholesterol homeostasis means prompt and strong responses by the cell to small variations in cholesterol; e.g., through cholesterol esterification or biosynthesis. Cells that are responsible for cholesterol uptake or synthesis, including liver cells, can also be used.

The cells used in the present assay can also be obtained from a wide variety of sources. For example, cells can be collected freshly from a specific source and/or stored sources. Cells can also be obtained from established or primary cell lines. In addition, all cells may be isolated from sources containing normal levels of cell membrane cholesterol and/or sources containing either abnormally high or abnormally low levels of cell membrane cholesterol. The cells may be plated or free in solution, including cells in media and/or biological fluids, either in vivo or in vitro. Screening can be performed in multi-well plates. Additionally, the present culture system can also be used to mimic different pathological states in cholesterol by using cells that have defective cholesterol levels or homeostasis. In this embodiment, as in others, it may be desirable to isolate cells that are known to have a certain cholesterol defect, such as a genetic defect.

One screening method involves contacting red blood cells with a test agent and measuring the cholesterol level or activity in the plasma membrane of the red blood cells with a lytic agent, such as amphotericin B, cholesterol oxidase, or saponin. When the cholesterol level or activity of the red blood cell is above a threshold level, the lytic agent causes disruption of the red blood cell membrane which causes the cells to leak hemoglobin into the surrounding media. This free hemoglobin can be easily detected via a photometer or simply by eye because it results in a consistent red solution in which the color does not settle out of solution. In contrast, unlysed red cells will settle out of the media and collect in the bottom of the container. As such, some embodiments can use conical shaped micro-well containers so that the red cells can settle and collect in a small area to provide a simple visual indication of cell lysis, for example by producing a central "button." This screen also provides a simple measure of the degree or percentage of cell lysis that occurs and provides a simple, straightforward primary method for measuring the effect a compound has on cholesterol levels because the red cells are economical and not complex.

Another screening method involves exposing fibroblasts to a test compounds and measuring the compound's effect on the fibroblast's plasma membrane cholesterol level with a lytic agent, for example amphotericin B, cholesterol oxidase or saponin. Fibroblasts have vigorous cholesterol homeostasis and thus provide a good indication of a compound's effect on live cells. As such, this system can provide an effective secondary screening method for following-up on promising compounds. One skilled in the art that this screening method can also be used as a primary screening method, if desired.

In the described methods, cell cholesterol level or activity can be increased or decreased prior to their use in the screening method. In this manner, the cholesterol level or activity of the cells or their components can be adjusted to a desired level. Examples of compounds which can decrease endogenous cholesterol levels are cyclodextrins, cyclophanes, phospholipid vesicles, lipid-free/lipid-poor apolipoproteins, reconstituted and native high density lipoprotein (HDL), cholesterol binding compounds, including certain antibiotics such as filipin, nystatin, digitonin, and/or streptolysin, and whole serum. As will be apparent to the skilled artisan, when antibiotics are used to reduce cholesterol levels antibiotics or amounts that result in cell lysis should not be used. Compounds that can be used to increase cholesterol levels include cyclodextrin-cholesterol complexes. Suitable cyclodextrins include beta-cyclodextrins and their derivatives, such as methyl-beta-cyclodextrin or hydroxy-propyl-β-cyclodextrin. Such compounds and techniques are discussed in Klein et al. Biochemistry. 1995 Oct. 24; 34(42):13784-93, Christian et al. J Lipid Res. 1997 November; 38(11):2264-72, Christian et al. J Lipid Res. 1999 August; 40(8):1475-82 and Rothblat et al. J Lipid Res. 1999 May; 40(5):781-96. Cellular cholesterol may also be depleted by culture in a media devoid of exogeneous cholesterol sources. Additionally, cholesterol biosynthesis may be inhibited by cholesterol inhibiting compounds. One group of these cholesterol inhibiting compounds includes the statins. Specifically, statins such as compactin, lovastatin and/or squalestatin block cholesterol production. Accordingly, cell cholesterol can be adjusted to a broad range of values, including increments of 10%, 20%, 25%, 30%, 50%, 75%, or more, up to two-fold or more.

These methods can further involve repeating the screening method one or more times, simultaneously, e.g. in a multi-well or parallel format, or subsequent to one another. In the repeats, one or more of the different parameters of the screening method, e.g. test compound, cell type, cholesterol level, cholesterol level measurement, etc., can be varied as desired. For example, an array of screens can be performed on different compounds simultaneously keeping all other conditions the same using a multi-well format. In this manner a large number of compounds, such as 5, 10, 25, 50, 100 or more, can be simultaneously screened for their cholesterol level modulating properties. In these and other formats, the same compound can be tested on different types of cells and/or on the same cell type pre-treated in different ways. One or more compounds can also be individually tested against a panel of two, three, four, five, six, seven, eight, nine, ten or more samples of the same type of cells that have different cholesterol levels, which levels can be staggered at regular or irregular intervals. These varied cholesterol levels can be achieved as described herein. Typically, cells of the same types used in the present methods will come from a single source and have similar or substantially homogeneous properties in order to simplify interpretation of assay results. Although such panel and array formats typically will use a multi-well format for simplicity, different containers can also be used for each sample.

The invention can be adapted for either low or high throughput screening of the effect of a test agent on the membrane cholesterol concentration, cholesterol activity or both of one or more cells. Cholesterol activity means the state of cholesterol beyond that constrained by membrane phospholipids such that it is more or less reactive with probes, such as cholesterol oxidase and cyclodextrins, and more or less capable of going to the endoplasmic reticulum and increasing or decreasing its cholesterol. Typically cholesterol activity is independent of cholesterol concentration in the membrane. Chemical activity of cholesterol is also discussed by Radhakrishnan et al., Proc Natl Acad Sci USA 2000 Nov. 7; 97(23):12422, and in other references cited herein. The screening method encompasses a method that is suitable, and is typically used, for assaying for a particular property or effect in a large number of test agents. However, individual test agents may be used. Typically, the screening method requires only a small amount of time for each test agent assayed; characteristically more than one test agent is assayed simultaneously (as in a 96-well microtiter plate), and preferably significant portions of the procedure can be automated. In fact, the present methods easily lend themselves to automation.

As described herein the effect of the test compound may be measured by any number of methods. In order to provide a gauge against which to measure the effect of the test agent, the results achieved with the compounds can be compared to a control, such control may include any assay done using the same experimental conditions but without the addition of the test agent or by comparing the results of the effect of the test agent with the total amount of cellular cholesterol. Preferentially, the methods used to measure the effect of a test agent include cell lysis and/or an increase in cell permeability caused by a lytic compound. However, other measures of cholesterol activity such as its transfer to cyclodextrin or changes in endoplasmic reticulum cholesterol can be used.

Figure 1:
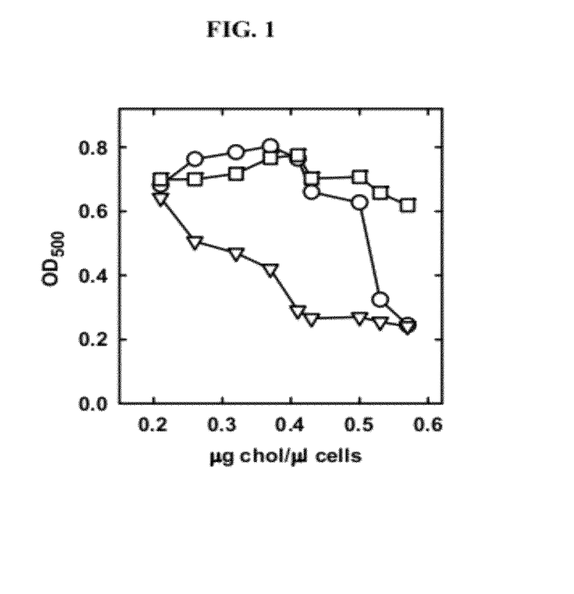

Typically, the present methods focus on cholesterol levels in the plasma membrane of cells because the vast bulk of the cell's cholesterol is associated with the plasma membrane. However, the homeostatic effectors that set the level of this cholesterol reside mostly in the endoplasmic reticulum (ER) and small variations in plasma membrane cholesterol near its physiological level can rapidly change ER cholesterol by a factor of 20 or more (FIG. 1). Without limiting the scope of the invention, it is believed that for regulatory purposes, the level of cholesterol in the plasma membrane sets the abundance of cholesterol in the ER which then makes the adjustments on behalf of the plasma membrane and the cell as a whole. In particular, a diverse set of regulatory mechanisms in the ER translate fluctuations in its cholesterol into homeostatic responses, restoring the plasma membrane to normal. The examples described below evidence that this homeostatic system not only responds to the level of plasma membrane cholesterol itself but also to alterations in the properties of the plasma membrane lipid bilayer. Thus, it is believed that the mechanism underlying this behavior is that the signal to the ER reflects the activity of the cholesterol in the plasma membrane rather than its absolute concentration. Radhakrishnan et al. Biochemistry. 2000 Jul. 18; 39(28):8119-24. The downstream consequences of a rise in plasma membrane cholesterol activity can result in an increase in the ER cholesterol pool size leading to a decrease in cell cholesterol minutes or hours later. In contrast, a fall in plasma membrane cholesterol activity can have the opposite effect. Accordingly, the present assay may identify compounds that modulate cell cholesterol levels by acting on the cholesterol activity of the plasma membrane and/or ER. In some embodiments, such compounds may raise the activity of the cholesterol in the plasma membrane, perhaps lodging in the plasma membrane bilayer, cause an increase in ER cholesterol, and thereby signal the cells to decrease cholesterol accumulation. Drugs of this type would reduce total body cholesterol by an entirely new mechanism. Additionally, because such drugs do not block cholesterol precursor molecules needed in the synthesis of other important cellular constituents, such as happens with statins, they will likely cause fewer side effects.

After a compound or test agent is identified as having a desired property, such as lowering cholesterol amounts, the test agent can be identified and then isolated, provided or chemically synthesized to produce a therapeutic drug. Thus, the present methods can be used to make drug products that modulate cellular cholesterol production and are useful for the therapeutic treatment of cholesterol disorders in vitro and in vivo. In some embodiments, such compounds will increase the cholesterol activity of a cell's plasma membrane or ER while in others the compounds will decrease the cholesterol activity of a cell's plasma membrane or ER. Such compounds can be used to treat cholesterol associated diseases and disorders, such as atherosclerosis and hypercholesterolemia. When used to treat such disorders the compounds will typically be provided or administered as a pharmaceutically acceptable composition.

The described screening methods have been used to identify compounds which modulate cholesterol activity, which can either upregulate or downregulate cholesterol production. As can be seen from the examples, octanol increases plasma membrane cholesterol activity in both red cells and human fibroblasts. In fact, in human fibroblasts, prolonged culture with octanol resulted in cholesterol reduction. The examples also demonstrate that in red blood cells similar effects to octanol are seen with physiologic membrane-intercalating alcohols such as ceramides and dyglycerides. Other fatty alcohols likely behave similarly, and a diverse class of such agents might be discovered by the assays described herein.

In contrast, the described screening methods identified that lysophosphatidylcholine has the opposite effect of octanol, ceramides, and diglycerides on certain cells and decreases plasma membrane cholesterol levels or activity which may result in increased cell cholesterol content. A diverse class of such agents might be discovered by the assays described herein.

Compounds that increase plasma membrane cholesterol activity, in the manner of octanol, ceramides and dyglycerides might also find use as an adjunct to the treatment of systemic fungal infections with polyene antibiotics such as amphotericin B, since a small reduction in the cholesterol content of the plasma membrane would protect the body cells from the toxicity of these sterol directed agents. Norman et al. Adv. Lipid Res., 14, 127-70. Compounds that can increase the sterol (typically, ergosterol) level of fungal cells, such as through selective targeting or fungal cell versus human cell specificity, may be used to make the fungal cells more susceptible to polyene antibiotic treatment. Similarly, individuals afflicted with bacterial infections producing sterol-directed toxins (e.g., streptolysin-d) might benefit from drugs that lower their plasma membrane cholesterol below the threshold required for the action of these toxins. Duncan et al. Biochim Biophys Acta, 603, 278-87.

The present invention also provides kits for carrying out the methods described. In one embodiment, the kit is made up of instructions for carrying out any of the depicted methods. The instructions can be provided in any intelligible form through a tangible medium, such as printed on paper, computer readable media, or the like. The present kits can also include one or more reagents, cells, buffers, culture media, culture media supplements, lytic compounds capable of causing lysis of one or more cells, specific cholesterol binding compound(s) for labeling cholesterol, chromatic or fluorescent dyes for staining or labeling the specific cholesterol binding compound(s), radioactive isotopes, and/or disposable lab equipment, such as multi-well plates. Examples of suitable kit components are described herein and set forth in the examples below. The main purpose of these kits is to readily facilitate implementation of the present methods.

This invention is further illustrated by the following non-limiting examples.

EXAMPLES

Example 1

Screen Using Red Blood Cell Lysis by Amphotericin B

Figure 2:
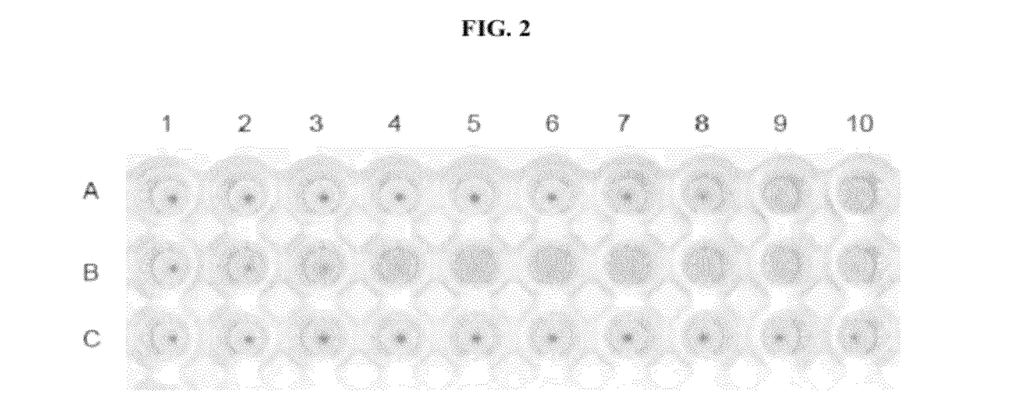

Human red cells (freshly drawn or from an outdated blood bank source) were washed and suspended in physiological buffer. The red cell's cholesterol content was lowered slightly (e.g., by 20%) with cyclodextrin (Steck et al., Biophys. J., 83, 2118-25, 2002) so that they would not be lysed by amphotericin B unless a favorable compound increased the activity of the cholesterol in their membrane. The cholesterol modified cells were placed in the wells of a microtiter plate and incubated for a few minutes at room temperature with octanol and lysophosphatidylcholine, which can be replaced with a battery of drugs (individually or in mixtures). Amphotericin B was then added and the plate incubated at room temperature for an hour. Cell lysis was scored by reading light scattering in a plate-reading photometer (FIG. 1) or, more simply, by letting the unlysed cells settle for an hour in conical wells and then assessing hemolysis by eye (FIG. 2). As seen in FIGS. 1 and 2, octanol favors amphotericin B lysis, suggesting that it increases the activity of membrane cholesterol while lysophosphatidylcholine has the opposite effect.

Discussion of Results

Polyene antibiotics such as amphotericin B are known to promote the disruption of cholesterol containing membranes. However, this action depends critically on the cholesterol level in the membrane (see the control curves, O - - - O, in FIGS. 1 and 2). The critical cholesterol content for lysis is close to the physiological level in human fibroblast plasma membranes, for the same reason that ER cholesterol responds dramatically near the physiological content of the plasma membrane. Without limiting the scope of the invention it is believed that the threshold observed in these assays reflects the saturation point of the membrane lipid bilayer and that cholesterol in excess of this point has a high activity and behaves in a special fashion. Drugs that raise the activity of plasma membrane cholesterol can therefore be recognized by their ability to increase cell susceptibility to amphotericin B lysis. Drugs of interest are those which potentiate cell lysis; presumably, by increasing the activity of plasma membrane cholesterol. Octanol is such a compound (∇ - - - ∇ in FIGS. 1 and 2). Conversely, agents that reduce cholesterol activity will protect against cell lysis; an example of which is lysophosphatidyl choline (o - - - o in FIGS. 1 and 2). Accordingly, this assay will be used to screen chemicals for their ability to raise the activity of plasma membrane cholesterol which should reduce the production of cholesterol in vivo.

Example 2

Screen Using Red Blood Cell Lysis with Cholesterol Oxidase

Figure 3:
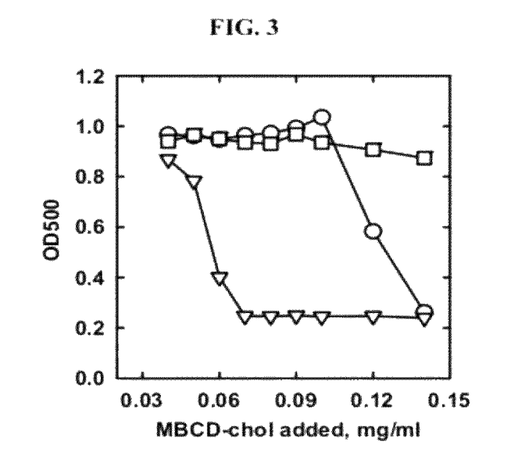
FIG. 3 shows the screening of red blood cell lysis using cholesterol oxidase. The cholesterol content of washed human red cells was varied with methyl-β-cyclodextrin-cholesterol complexes. The cells were distributed into a 96-well plate and incubated with saline (○), 0.2 μmol/well octanol (▽) or 1 μg/well lysophosphatidylcholine (□). Cholesterol oxidase (2 IU/ml) was added and the plate incubated for 1 h at 37° C. Turbidity (signifying intact cells) was determined in a plate-reading photometer as O.D. at 500 nm. Loss of turbidity reflects cell lysis.

The procedure used in this Example were the same as those for Example 1, except that cholesterol oxidase was substituted for amphotericin B. This example demonstrates that cholesterol oxidase also reports on membrane cholesterol activity. As with amphotericin B, the cholesterol oxidase enzyme scarcely acts upon cholesterol below a threshold that lies near the physiological level but vigorously oxidizes cholesterol once that threshold is reached. Lange et al. Biochim Biophys Acta, 769, 551-62. The oxidation of red cell membrane cholesterol leads to lysis. Promising agents can therefore be readily detected in a multiwell screen similar to that described above in Example 1. The results of this experiment are illustrated in FIG. 3.

Example 3

Screen Using Fibroblast Cell Lysis Detected with Cholesterol Oxidase

A human fibroblast cell line is grown in bulk culture and seeded into microtiter wells the day before experimentation. The fibroblast cells from the fibroblast cell line are rinsed and treated with octanol plus cholesterol oxidase as in Example 2. The increased level of plasma membrane cholesterol activity is detected in two ways. First, plasma membrane cholesterol activity is detected by susceptibility to cholesterol oxidase. Although cholesterol in human fibroblast is a poor substrate for cholesterol oxidase under standard conditions, it is readily oxidized when the plasma membrane cholesterol activity is increased; for example, by raising its concentration by 20-55% or by adding 0.1-1.0 mM octanol. Cell lysis caused by cholesterol oxidation can also be determined by measuring increased cell permeability using a plate fluorescence reader and the impermeable indicator of potassium ions, PBFI, or another indicator system.

Example 4

Assessment of Drug Action Using Fibroblasts and Amphotericin B

Figure 4:
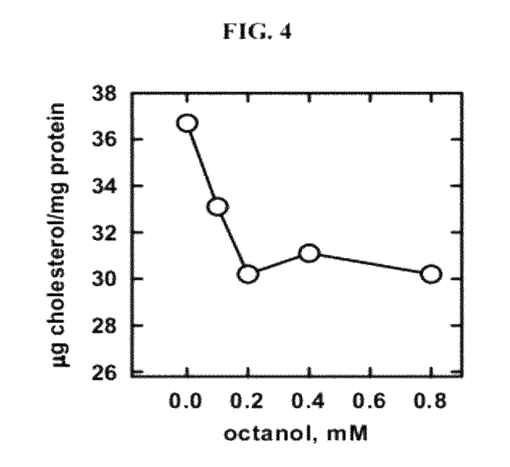
FIG. 4 depicts the effect of octanol on fibroblast cholesterol. Replicate flasks of fibroblasts were incubated for 24 h in growth medium with octanol. The cells were then assayed for cholesterol and protein.

The cultured cells described in Example 3 will be plated in microtiter wells and incubated with test compounds at 37° C. for two days to allow a full metabolic response. The drug will then be washed away, amphotericin B added to the wells and cell lysis followed from the leakage of potassium ions or another indicator, as above. Resistance to amphotericin B lysis will indicate that the objective has been achieved: the reduction of plasma membrane cholesterol in response to the test compound. Other polyene antibiotics (e.g., nystatin and filipin) will be tested in place of amphotericin B in order to discern their effects. In contrast to the screens described in the previous examples, which are used to identify compounds that raise the activity of membrane cholesterol, the present assay will measure the long-term effect of modulating cholesterol levels. Agents that increase plasma membrane cholesterol activity, when used as drugs, will signal cells to reduce their cholesterol accretion homeostatically. The reaction of fibroblasts with amphotericin B can then be used to detect the response of living cells to such drugs; namely, the homeostatic reduction of plasma membrane cholesterol. This is because agents that immediately raise the activity of plasma membrane cholesterol should, over time, lead to the reduction of the cholesterol content of the plasma membranes of living cells. This can be detected by their increased resistance to amphotericin B, which normally lyses these cells. The results for this experiment using octanol on fibroblasts is shown in FIG. 4.

Example 5

Figure 5:
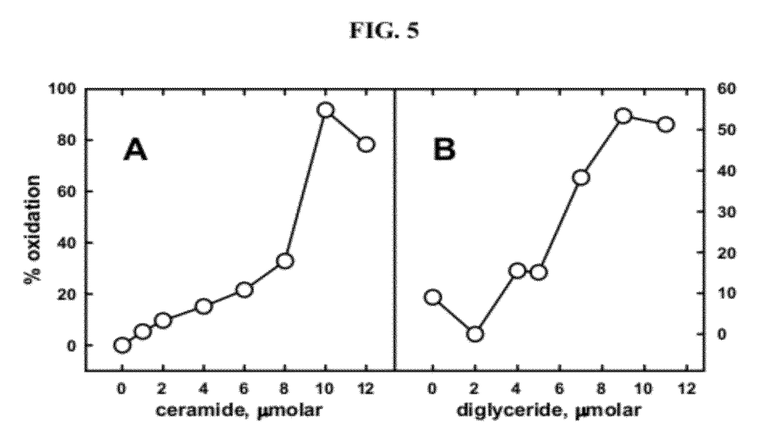
FIG. 5 shows the effect of ceramide and diglyceride on the oxidation of red cell membrane cholesterol by cholesterol oxidase. The red cell membranes were pretreated with ceramide or diglycerides and then treated with cholesterol oxidase for a hour. An increase in oxidation following cholesterol oxidase treatment signifies an increase in active cellular cholesterol.

Identifying Drugs by Screen Using Red Cell Membrane Lysis Detected with Cholesterol Oxidase Red cell membrane lysis is measured using cholesterol oxidase as set forth in the examples above. Prior to lysis, red cell membranes are treated with either differing amounts of a ceramide analog (0-12 µmolar) or differing amounts of a diglyceride analog (0-12 µmolar). The increased level of plasma membrane cholesterol activity is detected by susceptibility to cholesterol oxidase and measured as a % of oxidation. As demonstrated in FIG. 5, both ceramide and diglyceride increase the susceptibility of red cell cholesterol to oxidation.

Example 6

Drugs Identified by Screen Increase Lysis of Red Blood Cells with Saponin

Figure 6:
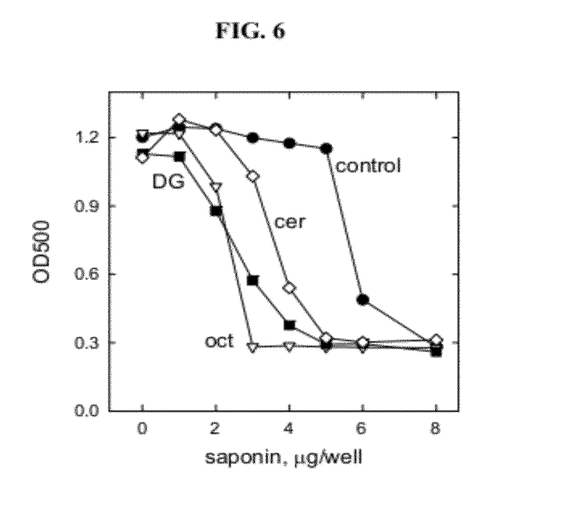
FIG. 6 demonstrates the effect of ceramide and diglyceride on the lysis of red blood cells by saponin. Red blood cells were pre-treated with either octanol, diglyceride, ceramide, or solvent before incubation with varying concentrations of saponin. The decrease in optical absorbance at 500 nm indicates increasing lysis.

Red cell membranes are treated with octanol, diglyceride, ceramide, or solvent before incubation with different concentrations of saponin (0-8 µg/well) for 30 minutes. Optical absorbance at $OD_{500}$ is measured. Decreased optical absorbance indicates increasing lysis by saponin. As demonstrated by FIG. 6, octanol (∇), diglyceride (■), and ceramide (◇) all increase lysis of red blood cells at lower concentrations of saponin as compared to control (♦).

Example 7

Follow-Up Testing

The properties of agents found to be desirable in these screens will be researched in the literature for possible serious adverse effects on cells or organisms in vitro or in vivo. In addition, these compounds should also be potent enough in vitro to suggest the possibility of therapeutic use in humans at a tolerable dose (e.g., less than one gram or 10 mg/kg body weight per day). The agents should be absorbable from the gastro-intestinal tract. Selected compounds will be further tested. In an initial simple characterization, agents of interest should show the following desired properties when applied to a variety of cell types grown in standard culture: reduced total cell and plasma membrane cholesterol, measured per cell, per unit protein or per phospholipid. Proof of principle is demonstrated for octanol in FIG. 4 and ceramide and diglyceride in FIG. 5 and FIG. 6. Biochemical tests will be used to verify that treated cells indeed incorrectly sense that they have excess cholesterol on board. For example, they should reduce their HMG-CoA reductase and LDL receptor levels. Treated cells should have near normal growth, as measured by the fractional rate of protein accretion. There should be near normal cell morphology and ultrastructural organization. The profile of other cell membrane lipids should also be essentially unchanged. Other evidence of cell injury (e.g., apoptosis) should be absent. Procedures: established methods will be used for the aforementioned measurements. See Reed, J. C, Ed., Methods in Enzymology Volume 322: Apoptosis (2000).

The present methods can involve any or all of the steps or conditions discussed above in various combinations, as desired. Accordingly, it will be readily apparent to the skilled artisan that in some of the disclosed methods certain steps can be deleted or additional steps performed without affecting the viability of the methods. Furthermore, as used herein, including specifically the language in the specification and the claims, use of "a" or "an" means "one" or "one or more."

As will be understood by one skilled in the art, for any and all purposes, particularly in terms of providing a written description, all ranges disclosed herein also encompass any and all possible subranges and combinations of subranges. Any listed range can be easily recognized as sufficiently describing and enabling the same range when broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," "more than" and the like include the number recited and refer to ranges that can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references disclosed herein are specifically incorporated by reference thereto. The following references are specifically incorporated.
1. Simons K, Ikonen E. (2000) How cells handle cholesterol. Science, 290, 1721-6.
2. Lange Y, Steck T L. (1996) The role of intracellular cholesterol transport in cholesterol homeostasis. Trends in Cell Biology, 6, 205-08.
3. Lange Y, Ye J, Rigney M, Steck T L. (1999) Regulation of endoplasmic reticulum cholesterol by plasma membrane cholesterol. J. Lipid Res., 40, 2264-70.
4. Radhakrishnan A, McConnell H M. (2000) Chemical activity of cholesterol in membranes. Biochemistry, 39, 8119-24.
5. Norman A W, Spielvogel A M, Wong R G. (1976) Polyene antibiotic-sterol interaction. Adv. Lipid Res., 14, 127-70.
6. Duncan J L, Buckingham L. (1980) Resistance to streptolysin O in mammalian cells treated with oxygenated derivatives of cholesterol. Cholesterol content of resistant cells and recovery of streptolysin O sensitivity. Biochim Biophys Acta, 603, 278-87.
7. Steck T L, Ye J, Lange Y. (2002) Probing red cell membrane cholesterol movement with cyclodextrin. Biophys. J., 83, 2118-25.
8. Lange Y, Matthies H, Steck T L. (1984) Cholesterol oxidase susceptibility of the red cell membrane. Biochim Biophys Acta, 769, 551-62.
9. Lange Y, Ye J, Steck T L. (2004) How plasma membrane cholesterol in excess of phospholipids regulates cholesterol homeostasis. Proc. Natl. Acad. USA, 101, 11664-67.

While preferred embodiments have been illustrated and described, it should be understood that changes and modifications can be made therein in accordance with ordinary skill in the art without departing from the invention in its broader aspects as defined in the following claims.

What is claimed is:

1. A method of screening compounds for cholesterol modulating activity, comprising:
   (a) providing an array that comprises two or more samples of the same type of cell in vitro under physiological conditions;
   (b) contacting one or more test agents with the cells;
   (c) determining whether the one or more test agents increase cholesterol activity in the plasma membrane of the cells; and
   (d) selecting those test agents that increase cholesterol activity, and determining if the selected test agents reduce HMG-CoA reductase and LDL receptor levels in cultured cells of the same cell type as the cells of steps (a)-(c).

2. The method of claim 1, wherein (c) comprises contacting the cells with lytic compound, wherein the lytic compound causes perforation or lyses of the membrane of the cells when the cholesterol activity of the membrane of the one or more cells reaches a level at or above a threshold cholesterol level.

3. The method of claim 2, wherein the lytic compound comprises a polyene antibiotic.

4. The method of claim 2, wherein the lytic compound comprises a lysophosphatide or cholesterol oxidase.

5. The method of claim 2, wherein the lytic compound comprises a bacterial toxin.

6. The method of claim 1, further comprising performing (b) and (c) one or more times with different test agents.

7. The method of claim 6, wherein the different test agents are screened simultaneously.

8. The method of claim 1, wherein the cells comprise one or more eukaryotic cells.

9. The method of claim 8, wherein the one or more eukaryotic cells comprise one or more mammalian cells.

10. The method of claim 8, wherein the one or more cells comprise one or more red blood cells.

11. The method of claim 8, wherein the one or more cells comprise one or more fibroblasts.

12. The method of claim 8, wherein the one or more cells comprise one or more human cells.

13. The method of claim 1, wherein the one or more cells have vigorous cholesterol homeostasis.

14. The method of claim 1, wherein (c) comprises measuring the permeability of the membrane of the one or more cells or the turbidity of the one or more cells.

* * * * *